(12) United States Patent
Verdoliva

(10) Patent No.: US 10,099,991 B2
(45) Date of Patent: Oct. 16, 2018

(54) PROCESS FOR THE SEPARATION OF DICARBOXYLIC ACIDS FROM AQUEOUS MIXTURES

(71) Applicant: NOVAMONT S.p.A., Novara (IT)

(72) Inventor: Antonio Verdoliva, Naples (IT)

(73) Assignee: Novamont S.p.A., Novara (IT)

( * ) Notice: Subject to any disclaimer, the term of this patent is extended or adjusted under 35 U.S.C. 154(b) by 0 days.

(21) Appl. No.: 15/105,002

(22) PCT Filed: Dec. 19, 2014

(86) PCT No.: PCT/EP2014/078747
§ 371 (c)(1),
(2) Date: Jun. 16, 2016

(87) PCT Pub. No.: WO2015/091952
PCT Pub. Date: Jun. 25, 2015

(65) Prior Publication Data
US 2016/0318838 A1    Nov. 3, 2016

(30) Foreign Application Priority Data
Dec. 20, 2013 (IT) .............................. NO2013A0009

(51) Int. Cl.
*C07C 51/42* (2006.01)
*C07C 57/13* (2006.01)

(52) U.S. Cl.
CPC .............. *C07C 51/42* (2013.01); *C07C 57/13* (2013.01)

(58) Field of Classification Search
CPC ................................. C07D 51/42; C07D 57/13
See application file for complete search history.

(56) References Cited

U.S. PATENT DOCUMENTS

| | | | | |
|---|---|---|---|---|
| 4,904,389 A | * | 2/1990 | Waldhoff | B01D 61/16 210/637 |
| 5,104,492 A | * | 4/1992 | King | C07C 51/48 203/15 |
| 6,143,532 A | | 11/2000 | Wenzel et al. | |
| 2011/0028759 A1 | | 2/2011 | Lum et al. | |

FOREIGN PATENT DOCUMENTS

| | | |
|---|---|---|
| CN | 102 476 987 | 5/2012 |
| CN | 102942472 | 2/2013 |
| GB | 2016453 A | 2/1979 |
| WO | WO 01/04337 A1 | 1/2001 |

OTHER PUBLICATIONS

International Search Report, PCT/EP2014/078747, dated Mar. 13, 2015.

* cited by examiner

*Primary Examiner* — Pancham Bakshi
*Assistant Examiner* — Mark R Luderer
(74) *Attorney, Agent, or Firm* — Finnegan, Henderson, Farabow, Garrett & Dunner, LLP

(57) ABSTRACT

This invention relates to a process for the separation of dicarboxylic acids from aqueous mixtures of $CV_8C_{24}$ mono- and dicarboxylic acids. In particular this invention relates to a process for the separation and purification of the said mixtures which uses an ultrafiltration stage.

11 Claims, No Drawings

PROCESS FOR THE SEPARATION OF DICARBOXYLIC ACIDS FROM AQUEOUS MIXTURES

This application is a national stage filing under 35 U.S.C. § 371 of International Application No. PCT/EP2014/078747, filed on Dec. 19, 2014, which claims priority of Italian Patent Application No. NO2013A000009 filed on Dec. 20, 2013, which the contents of these applications are each incorporated herein by reference.

FIELD OF THE INVENTION

This invention relates to a process for the separation of dicarboxylic acids from aqueous mixtures of long chain mono- and dicarboxylic acids. In particular this invention relates to a process for separating and purifying the said acids which includes an ultrafiltration stage.

TECHNICAL BACKGROUND $C_8$-$C_{24}$ dicarboxylic acids (also indicated individually or collectively in this application as "long chain dicarboxylic acids") are well known chemical intermediates widely used mainly as intermediates in the production of perfumes, lubricants, adhesives and as co-monomers for the production of various types of polymers such as for example aliphatic and aliphatic-aromatic polyesters of the diacid-diol type and polyamides of the diacid-diamine type.

At the present time these dicarboxylic acids are obtained by conventional chemical processes from various raw materials of both fossil and renewable origin. As far as processes of synthesis starting from raw materials of fossil origin are concerned, typical examples are the terminal oxidation reactions of linear hydrocarbons such as for example tridecane. As far as synthesis processes starting from raw materials of renewable energy are concerned, mention may be made by way of example of the ozonolysis of oleic acid to obtain azelaic acid and pelargonic acid, the synthesis of sebacic acid by the alkaline fusion of ricinoleic acid or metathesis reactions of monounsaturated fatty acids. The ever increasing search for new technologies having lesser environmental impact has also in recent years provided an incentive for the search for processes to obtain these long chain diacids using fermentation processes from corresponding hydrocarbons or linear monocarboxylic acids.

In all these processes, whether of the conventional chemical type or of the fermentative type, the dicarboxylic acids are generally obtained in a mixture with monocarboxylic acids which may derive from residual quantities of the starting raw material or be produced as intermediates in the synthesis reaction for the desired product.

Various methods for separating out and purifying the dicarboxylic acids so produced which provide for example for crystallisation, distillation, liquid/liquid extraction or settling have been proposed.

For example WO 01/04337 describes a process for the purification of fermentation broths for the recovery of carboxylic acids. The purification process provides for a first step in which the pH of the fermentation broth is adjusted to a value of 2 or less and a second step in which the broth at this pH is heated to a temperature of approximately 60-105° C. Under these conditions a three-phase system forms (an aqueous phase containing a few cell residues, an organic phase containing the carboxylic acids and a solid phase containing cell residues).

GB 2,016,453 instead describes a process for the purification of fermentation broths in which the broth is rendered basic, separating out a liquid phase containing the dicarboxylic acids. Subsequently the solution is acidified at pH<4, causing the dicarboxylic acids to precipitate out.

U.S. Pat. No. 6,143,532 describes a process for the purification of fermentation broths for the recovery of carboxylic acids. The purification process provides for a first step in which the pH of the fermentation broth is adjusted to a value of at least 6 and a second step in which the broth at this pH is heated to a temperature of approximately 60-75° C. Under these conditions a three-phase system forms (an upper clear aqueous phase, an intermediate organic phase containing the carboxylic acids, and a lower aqueous phase containing cell residues).

CN 102476987 discloses a process for the separation of dodecanedioic acid from a fermentation broth. The fermentation broth containing 10% of sodium salt of the dodecanedioic acid is fed to a ultrafiltration device for removing proteins and pigments. For obtaining dodecanedioic acid with sufficient purity degree the permeate containing the dicarboxylic acid is then extracted with an organic solvent, heated and acidified and then recovered by crystallization from the organic phase.

US 2011/028759 describes a process for recovery and purification of an organic acid such as lactic acid from a fermentation broth containing a salt form of the organic acid, which comprises the steps of subjecting the fermentation broth to one of ultrafiltration and microfiltration to form a first permeate, concentrating the first permeate to form a concentrated broth, subjecting the concentrated broth to a supported liquid membrane for extraction of lactic acid into a separate stream comprising an extracted solution, subjecting the extracted solution to activated carbon for colour removal, a cation exchange resin for demineralization, and an anion exchange resin for removal of anionic impurities.

SUMMARY OF THE INVENTION

However methods such as those described above do not make it possible to obtain the said acids with a high degree of purity in an economical way and there is therefore a need to develop new, simpler and improved methods for the separation and purification of long chain dicarboxylic acids which are sufficiently efficient and selective and at the same time are not economically unfavourable.

The object of this invention therefore lies in the provision of a new and improved process for the separation and purification of $C_8$-$C_{24}$ dicarboxylic acids which has appreciable and obvious advantages in comparison with the known processes described above.

In particular this invention relates to a process for the separation of $C_8$-$C_{24}$ dicarboxylic acids from an aqueous mixture containing $C_8$-$C_{24}$ monocarboxylic acids in addition to the said dicarboxylic acids through ultrafiltration, characterised in that during the said ultrafiltration the said $C_8$-$C_{24}$ mono- and dicarboxylic acids are in the aqueous mixture in the form of salts.

In another aspect, the present invention concerns the use of ultrafiltration for separating $C_8$-$C_{24}$ dicarboxylic acids from an aqueous mixture containing, in addition to said dicarboxylic acids, $C_8$-$C_{24}$ monocarboxylic acids, said process being characterized by the fact that during said ultrafiltration the $C_8$-$C_{24}$ mono- and dicarboxylic acids in the aqueous mixture are in salified form.

The process for the separation of $C_8$-$C_{24}$ dicarboxylic acids (long chain dicarboxylic acids) from an aqueous mixture containing $C_8$-$C_{24}$ monocarboxylic acids (long chain monocarboxylic acids) in accordance with the present invention comprises the stages of:

i. converting the $C_8$-$C_{24}$ mono- and dicarboxylic acids in the said aqueous mixture into a salt form, wherein said aqueous mixture is brought to a pH of 8 or greater, ii. ultrafiltering the aqueous mixture comprising the $C_8$-$C_{24}$ mono- and dicarboxylic acids in salt form originating from stage i.

DETAILED DESCRIPTION

In the meaning of this invention the term "long chain" identifies compounds having from 8 to 24 carbon atoms in the main chain. Typical examples of these long chain dicarboxylic acids are cis 9-octadecendioic acid, octadecandioic acid, hexadecandioic acid, tetradecandioic acid and brassylic acid. Typical examples of long chain monocarboxylic acids are instead oleic acid, stearic acid, palmitic acid, myristic acid and tridecanoic acid.

In this process ultrafiltration of the aqueous mixture makes it possible to separate the long chain monocarboxylic acids from the long chain dicarboxylic acids; it has in fact been discovered that during the ultrafiltration stage the monocarboxylic acids are selectively retained in the retentate while the dicarboxylic acids instead pass into the permeate, from which they can then be readily recovered. In a preferred embodiment this process provides for recovery (stage (iii)) of the dicarboxylic acids from the permeate obtained from the ultrafiltration stage.

Although the process according to this invention is particularly suitable for application downstream from fermentation processes, it remains understood that it is also possible to feed this process with aqueous mixtures containing long chain mono- and dicarboxylic acids originating from processes of any other type, such as for example those conventional chemical processes of the type described at the beginning of this application.

Furthermore the process according to this invention may also be used to separate mixtures of long chain dicarboxylic acids having chains of carbon atoms of different lengths from the aqueous mixtures containing them together with monocarboxylic acids.

Depending upon the origin of the aqueous mixtures, these may be subjected to one or more preliminary stages of pretreatment such as filtration, sterilisation, incubation or evaporation. For example in the case of aqueous mixtures originating from fermentation processes the aqueous mixture may first be treated in order to inactivate the microorganisms which are present during fermentation. This treatment may be applied using any physical or chemical process known to those skilled in the art, for example by incubating the mixture at high temperature, irradiating it with UV or gamma radiation or microwaves, or treating it with suitable chemical agents such as for example glutaraldehyde or peracetic acid. Choice of the type of inactivation treatment and its conditions are primarily dependent on the type of microorganism used in fermentation and those skilled in the art will therefore be able to identify the appropriate conditions for performing such inactivation.

Stage (i) of converting the mono- and dicarboxylic acids in the aqueous mixture into a salt is typically performed by adding a base, which may be of any type, for example an alkaline or alkaline earth hydroxide or mixtures thereof. By way of example, bases suitable for use in stage (i) of the process according to this invention are KOH and NaOH. The base may be added either in solid form or as aqueous solution, in the latter case adding a sufficiently concentrated solution to prevent excessive dilution of the mixture containing the long chain dicarboxylic acids. In the case of NaOH for example, 8 N aqueous solutions are suitable for this purpose.

Although the precise pH conditions at which formation of the salts of the mono- and dicarboxylic acids present in the mixture depends on the nature of the acids themselves and the other components which may be present in the aqueous mixture, it is well known that the formation of salts of mono- and dicarboxylic acids is favoured with increasing pH. Those skilled in the art will therefore be able to choose the quantity and type of base which is most appropriate for converting the acids present in the mixture into salts.

Stage (i) in this process is preferably carried out by adjusting the aqueous mixture to pH conditions in which the mono- and dicarboxylic acids are substantially wholly in the form of salts. The efficiency of separation is improved in this way, for reasons which will be illustrated below in this application. In the process of the present invention, stage (i) is performed by adjusting the aqueous mixture to a pH of 8 or more, preferably 10 or more, and even more preferably 12 or more. Nevertheless, in order to prevent the excessive use of base in this stage and to not render the subsequent stages in the process unnecessarily onerous, the pH of the aqueous mixture in stage (i) of the process may nevertheless be adjusted to pH values of 13 or less, preferably 12.5 or less. In an even more preferred embodiment of the process according to this invention stage (i) is therefore performed at a pH of between 8 and 13, preferably between 10 and 12.5 and even more preferably at a pH of between 12 and 12.5.

Salt-forming stage (i) in the process according to this invention may be carried out over a wide temperature range between 15 and 70° C. As is known, temperature also has an effect on the acid dissociation constant of the acids and therefore stage (i) of the process is generally advantageously performed at temperatures of 25° C. or above, preferably 30° C. or above, and more preferably in the range between 35 and 55° C.

Depending upon the various separation requirements and the nature of the acids which have to be separated those skilled in the art will therefore be in a position to balance the effect of pH and temperature on stage (i) of the process according to this invention. For example, in order to separate cis 9-octadecendioic acid from aqueous mixtures containing it together with oleic acid, stage (i) in the process is advantageously performed by adjusting the mixture to a pH of between 9 and 12.5 and a temperature between 35 and 55° C.

Preferably salt-forming stage (i) is performed with stirring, thus encouraging quick and uniform mixing of the base with the various components of the aqueous mixture. Advantageously, once addition of the base is complete, stirring of the aqueous mixture is maintained at a constant temperature for a time of between 10 and 30 minutes.

At the end of stage (i) the mono- and dicarboxylic acids are present in the mixture in salt form. The increase in the pH of the aqueous mixture may give rise to the formation of a solid suspension which if present is conveniently separated in order to assist the subsequent stage of ultrafiltration. By becoming deposited on the membranes of the filtering unit any solid suspension can in fact give rise to an increase in their operating pressure with a consequent reduction in performance. In the case of aqueous mixtures originating from fermentation processes this separation phase also makes it possible to remove any cell residues present in the aqueous mixture. In the meaning of this invention the term "solid suspension" also means colloidal dispersions, slurries and any fraction having a sufficiently high density to separate out from a supernatant. In one embodiment of the process according to this invention the solid suspension present at the end of stage (i) is therefore separated from the aqueous mixture before ultrafiltration stage (ii).

In this separation phase the aqueous mixture originating from salt-forming stage (i) can be subjected to one or more treatments selected from settling, centrifuging, filtration, microfiltration, other suitable solid/liquid separation techniques and combinations thereof. For example, the stage of separating out the solid suspension may provide for the combined use of centrifuging and microfiltration, feeding the aqueous mixture in which the aqueous suspension is present to a centrifuge and subsequently microfiltering the supernatant separated out after centrifuging. The choice of the type of equipment, their combinations and their method of operation will primarily depend on the quantity and nature of the solid suspension which has to be separated out.

In this process the stage of ultrafiltration of the aqueous mixture makes it possible to separate out the monocarboxylic acids from the long chain dicarboxylic acids. Without being hereby bound to any specific theory it is considered in fact that the long chain monocarboxylic acids in salt form present in the aqueous mixture form colloidal aggregates which are held back in the retentate during the ultrafiltration stage. Because of the amphiphilic nature of the said monocarboxylic acids in salt form these aggregates are felt to be of a micellar nature. As is known, the formation of micelles is a phenomenon which depends on many factors, among which the main ones are the concentration of the compounds having an amphiphilic structure and the temperature of the medium.

In the process according to this invention, depending upon the initial concentration of the mono- and dicarboxylic acids in the aqueous mixture, it is also possible to provide one or more stages of evaporation of the aqueous mixture or the various intermediate fractions prior to the ultrafiltration stage in order to remove part of the water present, thus helping not only to minimise the volumes of the equipment, but also to render the ultrafiltration stage more efficient.

The ultrafiltration stage in this process may be performed over a wide temperature range between 15 and 70° C. As is known, temperature also has an effect on the acid dissociation constant of the acids and therefore this ultrafiltration stage is generally advantageously performed at temperatures of 25° C. or above, preferably 30° C. or above, and more preferably within the range between 35 and 55° C. In a preferred embodiment of the process according to this invention ultrafiltration stage (ii) is performed at the same temperature as salt-forming stage (i).

Any ultrafiltration technique which uses any filtering units provided with a semi-permeable membrane which is for example tubular, with a spiral hollow fibre of the "plate and frame" type and which operates using a flow tangential or perpendicular to the surface of the membrane, may be used for the ultrafiltration stage in this process. With regard to the filtering membranes which are to be used in the ultrafiltration stage, any permeable membranes of cellulose acetate, derivatives of cellulose acetate such as cellulose acetobutyrate, and synthetic polymers such as for example polypropylenes, polyamides, polyimides, PVDF (polyvinyledene fluoride), PAN (polyacrylonitrile), PES (polyether sulfone) and ceramic may be used. Preferably semi-permeable membranes of cellulose acetate or polyether sulfone are used. The porosity of the membranes has an effect on the ultrafiltration performance and the efficiency of separation. In general, in order to retain monocarboxylic acids having a main chain with 14 or fewer carbon atoms in the retentate it is preferable to use membranes having a porosity of 5 kDa or less, while for monocarboxylic acids having more than 14 carbon atoms in the main chain even membranes having a porosity of 10 kDa or more may be used.

The choice of temperature, transmembrane pressure and other operating conditions under which the ultrafiltration stage is performed is determined mainly by the viscosity of the aqueous mixture fed to it and the type and porosity of the membrane used. In general the viscosity of the aqueous mixture will be greater when working at low temperatures and higher feed pressures must be used for the same membrane.

As the ultrafiltration stage proceeds the viscosity of the aqueous mixture and the transmembrane pressure naturally tend to increase and the separation efficiency tends to decrease. This makes it necessary to use increasingly greater pressures, which if they are too high may damage the filtering unit and compromise the efficiency of the process. In order to prevent the use of excessively high pressures it is possible to use so-called diafiltration, feeding one or more aliquots of a make-up solution which compensates for the portion of the aqueous mixture which has permeated through the membrane.

Diafiltration may be performed either continuously or discontinuously. In the discontinuous system the aqueous mixture upstream of the membrane is progressively concentrated through the effect of the product permeating through the membrane. To compensate for the permeated solution one or more aliquots of make-up solution are added to the aqueous mixture retained in the retentate, and further ultrafiltrations are then performed. Preferably, in the process according to this invention, not more than 6 aliquots of make-up solution are added to prevent excessive dilution of the permeate with the long chain dicarboxylic acids.

Diafiltration may also be performed continuously. In this case the make-up solution is continuously added to the retentate in such a way as to prevent excessive concentration of the mixture upstream of the filtering membrane and the consequent increase in pressure which is necessary in order to perform ultrafiltration.

The make-up solution is typically represented by a solution having a pH which is the same as that of the aqueous mixture, which will not therefore alter the degree of salt forming in the mono- and dicarboxylic acids present therein.

Before the stage in which the dicarboxylic acids are recovered the permeate containing the long chain dicarboxylic acid is advantageously acidified. Acidification comprises restoring the long chain dicarboxylic acids to the undissociated form and aiding their recovery from the rest of the permeate. This acidification is advantageously performed by using strong acids such as for example HCl or $H_2SO_4$ or mixtures thereof. Aqueous solutions of the said strong acids which advantageously should be sufficiently concentrated to prevent excessive dilution of the permeate can then also be used for acidification. This in fact renders subsequent recovery of the long chain dicarboxylic acids more onerous.

Acidification is typically performed with stirring, thus assisting quick and uniform mixing of the strong acid with the components of the permeate. Advantageously, once the addition of acid is complete the permeate is kept stirred at a constant temperature for a time of between 5 and 10 minutes.

The stage of recovery of the long chain dicarboxylic acids is advantageously performed through one or more separation treatments for example by distillation, liquid/liquid extraction, adsorption, precipitation, crystallisation or combinations thereof. Those skilled in the art will be capable of choosing the appropriate method of recovery depending upon the concentration and the type of the dicarboxylic acids present in the eluate.

In the case of permeates containing several long chain dicarboxylic acids those skilled in the art will be capable of recovering the individual acids separately, making opportune use of their chemical and physical properties on the basis of the separation treatments mentioned above. For example, depending upon the volatility characteristics of the said acids, it is well known that acids having higher volatility can be separated from acids having progressively greater volatility at different heights in the distillation column.

Preferably the recovery stage in the process according to this invention is carried out by means of a treatment precipitating out the dicarboxylic acids from the permeate obtained in the ultrafiltration stage in the process. This precipitation treatment is advantageously performed (iii-a) by causing the dicarboxylic acids to precipitate out according to any of the methods known to those skilled in the art and subsequently (iii-b) separating out the precipitated dicarboxylic acids from the remaining permeate. Precipitation of the dicarboxylic acids may for example be achieved by progressively concentrating the acids through evaporating the water in the permeate or reducing their solubility, for example by lowering the temperature of the permeate. It is also possible to combine several methods of precipitation, for example first concentrating the acids by evaporating water from the permeate and subsequently reducing the solubility by lowering the temperature of the permeate.

The precipitate obtained is then separated from the remaining permeate by any of the methods known to those skilled in the art, for example by filtration or centrifuging, or using any combination of these methods.

In the case of permeates containing several long chain dicarboxylic acids those skilled in the art will be able to conduct the precipitation treatment in such a way as to recover the individual dicarboxylic acids separately, for example, on the basis of the solubility characteristics of the said acids, precipitating out and separating the acids having lesser solubility and repeating the treatment for acids having progressively greater solubility.

In a preferred embodiment of the process according to this invention the long chain dicarboxylic acids are recovered by precipitation treatment from a permeate originating from the ultrafiltration stage which has previously been acidified. Depending upon their concentration in the permeate and their solubility in water the long chain dicarboxylic acids passing from the salt form to the undissociated form can in fact begin to precipitate out even during acidification, thus accelerating and aiding the subsequent stage of recovery by precipitation.

In a particularly preferred embodiment of the process according to this invention the permeate originating from the ultrafiltration stage in this process is acidified to a pH between 2 and 3, preferably between 2 and 2.2, and subsequently cooled, for example to 4° C. for a period of approximately 2 hours, so as to cause the long chain dicarboxylic acids to precipitate out.

The long chain dicarboxylic acids recovered from the permeate can then be subsequently purified (stage (iv)). This purification stage may be performed by one or more treatments selected from desiccation, lyophilisation, distillation, liquid/liquid extraction and adsorption crystallisation. In the case of mixtures of long chain dicarboxylic acids those skilled in the art will be capable of performing stage (iv) in order to recover the individual dicarboxylic acids separately, making opportune use of their physical and chemical properties on the basis of the separation treatments mentioned above.

The invention will now be described through some examples which are intended to be illustrative in nature and which do not restrict its scope.

EXAMPLES

Example 1

Approximately 9 liters of sterilised fermentation broth deriving from the fermentation of a culture medium containing oleic acid using a yeast of the Candida species were incubated in a thermostatted bath for 60 minutes at 50° C. The fermentation broth, which comprised an aqueous mixture containing 1.5 g/L of residual oleic acid and 37.5 g/l of cis 9-octodecendioic acid, was then stirred at 250 rpm at a temperature of approximately 50° C. and an 8 N NaOH aqueous solution was then added to this to achieve a pH of 12. The broth so obtained was kept stirred at 250 rpm for 30 minutes at 50° C. Subsequently the broth rendered basic in this way was centrifuged at 8000 rpm for 20 minutes at approximately 23° C. The supernatant was separated out and subjected to microfiltration on a Sartopore 2 filter. On completion of the microfiltration the total volume of basic and microfiltered broth was approximately 9 liters.

The basic and microfiltered broth was then subjected to tangential ultrafiltration using a Mod. Cogent M1 filter unit provided with a PES Millipore membrane having a porosity of 10 kDa and a total filtering surface area of 0.33 $m^3$ operating under the following conditions:
feed pressure 2.6-3.0 bar
retentate pressure 0.6 bar
retentate flow 2.0 L/min
trans membrane pressure: 2.3 bar
temperature 25° C.

The ultrafiltration process was carried out using discontinuous diafiltration for which a 10 mN NaOH aqueous solution was used as the make-up solution. Approximately 2 liters of make-up solution were added when the retentate had reached approximately 25-20% of its initial volume (approximately 2 liters). Addition of the make-up solution was repeated another four times (five aliquots of 2 liters of make-up solution were added in all) repeating the addition whenever the volume of the retentate again reached 25-20% of the initial volume (approximately 2 liters). The various permeate fractions were pooled, obtaining a volume of approximately 18 liters, and analysed to determine the oleic acid and cis 9-octadecendioic acid contents through gas chromatography under the following conditions:
Gas chromatograph: ThermoFinnigan Focus GC;
Detector: FID at T 340° C.;
Column: ZEBRON ZB-5Msi (15 m×ID 0.25 mm×film thickness 0.25 μm);
Initial T: 90° C. isocratic for 2 min;
Temperature rise: 12° C./min;
Final T: 320° C. isocratic for 5 min;
Injector T: 300° C.;
Injector type: splitless;
Injected volume: 1 μl;
Carrier gas: $N_2$;
Carrier gas flow: 1.2 ml/min.

The same analysis was performed on the retentate (approximately 1.8 liters). The results are shown in Table 1

TABLE 1

|  | Oleic acid (g/L) | cis 9-octadecenedioic acid (g/L) |
|---|---|---|
| Retentate | 7.6 | 1.3 |
| Permeate | not detectable | 16.5 |

8 N HCl was then added to the permeate with constant stirring at 250 rpm until a pH of approximately 2 was reached, thus bringing about precipitation of the cis 9-octadecendioic acid. The acidified permeate was then stirred for approximately 10 minutes and held at 4° C. for 12 hours. The cis 9-octadecendioic acid was then separated from the rest of the permeate by filtration on filter paper.

The filtrate was then purified again by washing with 50 mM HCl obtaining a total yield of approximately 90% of cis 9-octadecendioic acid in comparison with the quantity present in the fermentation broth.

Example 2

The following four aqueous mixtures containing mono- and dicarboxylic acids were prepared:
Aqueous mixture 1: 250 mg of oleic acid and 250 mg of cis 9-octadecendioic acid in 40 ml of water;
Aqueous mixture 2: 250 mg of palmitic acid and 250 mg of hexadecandioic acid in 40 ml of water;
Aqueous mixture 3: 250 mg of myristic acid and 250 mg of tetradecandioic acid in 40 ml of water;
Aqueous mixture 4: 250 mg of tridecanoic acid, 250 mg of brassylic acid in 40 ml of water.

For preparation of the four aqueous mixtures the mono- and dicarboxylic acids were dispersed in water and, in order to accelerate the process of dissolving the said acids, the whole was heated to approximately 50° C. with stirring until the mixtures appeared clear. The pH of the aqueous mixtures was then raised to a value of 12.3 by adding an aqueous solution of 8N KOH, again with stirring. The mixtures were subsequently kept stirred at 50° C. for approximately 20 minutes.

3 ml of each of the mixtures then underwent a centrifugal ultrafiltration test at T=25° C. using a HERAEUS Sepatech MEGAFUGE 1.0R centrifuge and suitable ultrafilters having different porosities (FES Vivaspin ultrafilters of 5, 10, 30 and 50 kDa produced by Sartorius and regenerated cellulose Ultra ultrafilters of 3 kDa produced by Amicon) operating at a centrifuging speed of 4000 rpm.

The permeate was analysed by gas chromatography under the same conditions as in Example 1 to determine the quantities of mono- and dicarboxylic acids present. Tables 2-5 show the percentages by weight of the mono- and dicarboxylic acids in the permeates so obtained in comparison with the quantities present in the starting aqueous mixtures.

TABLE 2

Ultrafiltration tests on Aqueous Mixture 1

| Membrane porosity | Oleic acid | cis 9-octodecenedioic acid |
|---|---|---|
| 10 | 0 | 100 |
| 30 | 0 | 100 |
| 50 | 20 | 100 |

TABLE 3

Ultrafiltration tests on Aqueous Mixture 2

| Membrane porosity | Palmitic acid | Hexadecandioic acid |
|---|---|---|
| 5 | 0 | 100 |
| 10 | 0 | 100 |
| 30 | 0 | 100 |
| 50 | 30 | 100 |

TABLE 4

Ultrafiltration tests on Aqueous Mixture 3*

| Membrane porosity | Myristic acid | Tetradecandioic acid |
|---|---|---|
| 5 | 0 | 100 |
| 10 | 5 | 100 |

*ultrafiltration carried out at 30° C.

TABLE 5

Ultrafiltration tests on Aqueous Mixture 4

| Membrane porosity | Tridecanoic acid | Brassylic acid |
|---|---|---|
| 3 | 0 | 100 |
| 5 | 4 | 100 |
| 10 | 10 | 100 |

Example 3

In order to investigate the effect of the pH value and of the temperature during the ultrafiltration the following 10 ultrafiltration tests were prepared in the following conditions.

|  | pH of ultrafiltration | | | | |
|---|---|---|---|---|---|
| T of ultrafiltration | 12 | 10 | 9 | 8 | 7 |
| 20° C. | ● | ● | ● | ● | ● |
| 30° C. | ● | ● | ● | ● | ● |

10 aqueous mixtures containing 10 mg/ml of oleic acid and 10 mg/ml of cis 9-octadecendioic acid and different pH values were prepared starting from a mother solution prepared according to the following procedure: 20 g of cis 9-octadecendioic acid were weighted and dissolved in 1400 ml of aqueous NaOH 0.5 N under stirring at 50° C., monitoring and maintaining the pH in the range of 12.0-12.5 by adding dropwise aqueous NaOH 8 N. When dissolution of cis 9-octadecendioic acid was completed 20 g of oleic acid were added, then leaving the solution under stirring at 50° C. for 15 minutes and maintaining the pH in the range of 12.0-12.5 by adding dropwise aqueous NaOH 8 N. The solution was then brought to about 1800 ml of total volume by adding water and aqueous NaOH 0.5 N in order to maintain a pH of 12. 15 aliquots of the mother solution were taken and diluted to 100 ml by adding different amounts of aqueous HCl 1 N to adjust the pH to the desired value. Each aqueous mixture was then brought to the desired temperature for the ultrafiltration and held at that temperature for 10 minutes under stirring.

The aqueous solutions presented a very low degree of turbidity and were fed to an ultrafiltration step using a HERAEUS Sepatech MEGAFUGE 1.0R centrifuge and ultrafilters in regenerated cellulose TFF PXC010C50 ultrafilters of 10 kDa produced by Millipore (50 cm$^2$ of filtrating area) operating at a centrifuging speed of 4000 rpm. The ultrafiltration process was carried out on 50 ml of the aqueous solutions, using discontinuous diafiltration for which a 10 ml of 10 mN NaOH aqueous solution was used as the make-up solution, which was added when the retentato had reached approximately 25-20% of its initial volume. Addition of the make-up solution was repeated another four times (five aliquots of 50 ml of make-up solution were added in all) repeating the addition whenever the volume of the retentate again reached 25-20% of the initial volume. The various permeate fractions were put together and analysed to determine the oleic acid and cis 9-octadecendioic acid contents through gas chromatography under the same conditions as in Example 1. Tables 6-7 show the percentages by weight of the mono- and dicarboxylic acids in the permeates so obtained in comparison with the quantities present in the starting aqueous mixtures.

TABLE 6

Ultrafiltration at 20° C.

| | pH | | | | |
|---|---|---|---|---|---|
| | 12 | 10 | 9 | 8 | 7 |
| cis 9-octadecendioic acid (%) | 98 | 93 | 54 | 47.5 | <10 |
| oleic acid (%) | 0.01 | 0.01 | 0.01 | 0.01 | 0.01 |

TABLE 7

Ultrafiltration at 30° C.

| | pH | | | | |
|---|---|---|---|---|---|
| | 12 | 10 | 9 | 8 | 7 |
| cis 9-octadecendioic acid (%) | 98 | 98 | 90 | 50 | <10 |
| oleic acid (%) | 0.2 | 0.2 | 0.2 | 0.2 | 0.01 |

The invention claimed is:

1. A method for separating $C_8$-$C_{24}$ dicarboxylic acids from an aqueous mixture containing $C_8$-$C_{24}$ dicarboxylic acids and $C_8$-$C_{24}$ monocarboxylic acids, the method comprising:
   (i) adding a base to adjust the pH of the aqueous mixture to a pH of about 8 or greater, wherein the addition brings into salified form the $C_8$-$C_{24}$ mono- and dicarboxylic acids; and
   (ii) ultrafiltering the aqueous mixture from step (i) to separate the $C_8$-$C_{24}$ dicarboxylic acids from the $C_8$-$C_{24}$ monocarboxylic acids.

2. The method of claim 1, wherein the base is chosen from an alkaline hydroxide, an alkaline earth hydroxide, and mixtures thereof.

3. The method of claim 2, wherein the base is added in a solid form or in the form of an aqueous solution.

4. The method of claim 1, wherein the pH of the aqueous mixture in step (i) is in a range from about 8 to about 13.

5. The method of claim 1, wherein step (i) is performed at temperature ranging from about 15° C. to about 70° C.

6. The method of claim 1, further comprising the step of subjecting the aqueous mixture to one or more solid/liquid separation treatments after step (i) and prior to the step (ii).

7. The method of claim 1, wherein step (ii) is performed at temperature ranging from about 15° C. to about 70° C.

8. The method of claim 1, wherein step (ii) is performed by diafiltration.

9. The method of claim 1, wherein the $C_8$-$C_{24}$ dicarboxylic acids are present in the permeate originating from step (ii).

10. The method of claim 9, wherein the permeate containing the $C_8$-$C_{24}$ dicarboxylic acids is acidified.

11. The method of claim 10, wherein the $C_8$-$C_{24}$ dicarboxylic acids are recovered from the acidified permeate by precipitation.

* * * * *